United States Patent
DiGeronimo (10) Patent No.: US 12,403,205 B2
(45) Date of Patent: Sep. 2, 2025

(54) SYSTEM AND METHOD FOR ULTRAVIOLET STERILIZATION OF FLUIDS

(71) Applicant: Dover Brook Associates, Chester, NY (US)

(72) Inventor: Michael John DiGeronimo, Chester, NY (US)

(73) Assignee: Dover Brook Associates, Chester, NY (US)

( * ) Notice: Subject to any disclaimer, the term of this patent is extended or adjusted under 35 U.S.C. 154(b) by 720 days.

(21) Appl. No.: 17/720,910

(22) Filed: Apr. 14, 2022

(65) Prior Publication Data

US 2023/0330282 A1   Oct. 19, 2023

(51) Int. Cl.
*A61L 2/10* (2006.01)

(52) U.S. Cl.
CPC ............ *A61L 2/10* (2013.01); *A61L 2202/11* (2013.01)

(58) Field of Classification Search
CPC ................................. A61L 2/10; A61L 2202/11
See application file for complete search history.

(56) References Cited

U.S. PATENT DOCUMENTS

| | | | |
|---|---|---|---|
| 10,131,529 B2 | 11/2018 | Jersey et al. | |
| 10,639,387 B2 | 5/2020 | Bonutti et al. | |
| 2017/0369334 A1 | 12/2017 | Park | |

FOREIGN PATENT DOCUMENTS

| | | |
|---|---|---|
| CA | 2574005 A1 | 7/2008 |
| CN | 103945712 A | 7/2014 |
| CN | 111107749 A | 5/2020 |
| DE | 10 2015 008396 A1 | 1/2017 |
| DK | 179693 B1 | 3/2019 |
| FR | 3 045 409 A1 | 6/2017 |
| WO | 2008/113128 A1 | 9/2008 |
| WO | 2016171608 A1 | 10/2016 |
| WO | 2018026008 A1 | 2/2018 |

OTHER PUBLICATIONS

Extended European Search Report in co-pending EP Application No. 23166007.7, mailed May 22, 2023, 6 pages.
Kurtz, Steven M., et al. "Future young patient demand for primary and revision joint replacement: national projections from 2010 to 2030." Clinical orthopaedics and related research vol. 467, 10 (2009): 2606-12. doi:10.1007/s11999-009-0834-6.
Chinese Office Action in CN Application No. 2023104003222.4, mailed May 24, 2025, an English translation attached hereto (12 pages).

*Primary Examiner* — Sean E Conley
(74) *Attorney, Agent, or Firm* — Leason Ellis LLP (57) ABSTRACT

A reactor for sterilizing a stream of fluid comprises of a frame structure having a longitudinal dimension and a plurality of UV plate reactors that are removably insertable into the frame structure in a series extending along the longitudinal dimension of the frame structure, each of the plurality of UV plate reactors including a single channel or a plurality of multiple channels of a selected diameter into which the stream of fluid is transported, and at least one ultraviolet light source having a selected radiant flux is coupled to one or more of the channels. The diameter of the plurality of channels and the radiant flux of the ultraviolet light source are selected so as to provide a precise dosage of ultraviolet radiation to the stream of fluid in a confined space of the plurality of channels so as to obtain sterilization of the stream of fluid.

12 Claims, 10 Drawing Sheets

SYSTEM AND METHOD FOR ULTRAVIOLET STERILIZATION OF FLUIDS

FIELD OF THE DISCLOSURE

The present disclosure relates to the field of sterilization treatment of water and other fluids using ultraviolet (UV) light irradiation. More particularly, the present disclosure relates to a system and method of UV sterilization of fluids using a plate and frame UV reactor that exposes fluids to UV radiation using a controlled depth and surface area.

BACKGROUND OF THE DISCLOSURE

Ultraviolet (UV) radiation has been used for sterilization purposes for some time. A particular high-frequency band of UV radiation, known as UVC, is particularly effective at sterilization. Multiple studies have shown that when microorganisms such as bacteria, viruses, molds, yeasts, and protozoa, are exposed to deep UVC radiation in the spectral wavelength range of 100 nm to 280 nm, it is absorbed by DNA, RNA, and proteins. More specifically, it is some of the amino acids which make up the proteins that actually absorb the UV light. This can disrupt the cell membrane of microorganisms, resulting in their death. Absorption of UVC by DNA can lead the creation of thymine-thymine dimerization and death of the organisms. If enough strands are inactivated, DNA/RNA replication process is disrupted, and the cells cannot replicate.

Due to its advantages, UV irradiation techniques have been used in the food industry for some time for disinfection/sterilization process applications. It is typically the preferred treatment method because, with irradiation treatment, no chemicals are introduced to treated liquid substance. Additionally, the irradiation process does not produce unfavorable by-products.

A crucial parameter for microbial sterilization is the UV dose, which is the amount of UV radiation a microbe is exposed to. The dose depends on the intensity of UV radiation and the time duration of exposure. A number of biological studies have produced widely accepted typical UV dose requirements for most common target microbes in disinfection. For example, to achieve a 3 log reduction (99.9 percent) of B. Subtillus (ATCC 6633) requires a 60 mJ/cm$^2$ dose.

To date, conventional UV systems have suffered from inefficiencies due to UV exposure that is inadequate and inconsistent. What is therefore needed is a system and method for UV sterilization that provides sufficient and consistent UV dosing.

SUMMARY OF THE DISCLOSURE

In one aspect, the present disclosure describes a reactor for sterilizing a stream of fluid. The reactor comprises a frame structure having a longitudinal dimension and a plurality of UV plate reactors that are removably insertable into the frame structure in a series extending along the longitudinal dimension of the frame structure, each of the plurality of UV plate reactors including at least one channel of a selected diameter into and through which the stream of fluid is transported, and at least one ultraviolet light source having a selected radiant flux is coupled to one or more of the plurality of channels.

In another aspect, the present disclosure describes a method for sterilizing a stream of fluid. The method includes transporting the fluid stream through a reactor having a series of modular UV plates with a single channel or multiple channels arranged along a longitudinal dimension, each UV plate reactor including a single or multiple channels of a selected diameter and irradiating the stream of fluid with ultraviolet radiation of a selected radiant flux as the fluid stream is transported through the plurality of channels of the UV plate reactors. The diameter of the plurality of channels and the radiant flux of the ultraviolet light source are selected so as to provide a precise dosage of ultraviolet radiation to the stream of fluid in a confined space of the plurality of channels so as to achieve sterilization of the stream of fluid.

In another aspect, the dosage and stream flow characteristics can be selected to optimize sterilization of the stream of fluid.

These and other aspects, features, and advantages can be appreciated from the following description of certain embodiments of the invention and the accompanying drawing figures and claims.

DESCRIPTION OF CERTAIN EMBODIMENTS OF THE DISCLOSURE

The present disclosure describes a system and method for sterilization of fluids, such as water or liquid food items that may or may not contain organic compounds using ultraviolet (UV) radiation, and preferably UVC radiation. The entire UV radiation spectrum covers the wavelength range of 100 nm to 400 nm, and is divided into three regions, the shortest of which being UVC within the range of 100 nm to 280 nm, emitting highly effective sterilization power. UVC germicidal wavelength at 260 mm is the most effective to kill harmful microorganisms in the air, water, and on surfaces.

Embodiments of the system disclosed herein comprise a reactor ("UV reactor") that comprises a series of modular plate reactors. In some embodiments, the plate reactors include a stainless-steel housing, a quartz crystal sleeve, a UV radiation source, and at least one channel through which the fluid to be sterilized is transported. The steel housing and quartz sleeve separate the ultraviolet radiation source from the stream of fluid. Within the UV reactor, the fluid stream is directed through channels of a series of plate reactors. Fluid circulates into and out of the UV reactor through an inlet and an outlet under control of a VFD (Variable Frequency Drive) pump. The ultraviolet sterilization method does not require the removal of oxygen from the fluid prior to irradiation. The method additionally also does not require a temperature range limit for the liquid during sterilization. The disclosed system further improves on conventional methods by controlling the precise dimensions of the fluid stream desired to be sterilized and the amount of UV light flux that is directed onto the fluid stream.

The ultraviolet sterilization method uses specific UV light emitting diodes (LEDs) to irradiate the liquids, but the adaptations of non-LED lights can be employed. Arrays of several LEDs are installed on each of the plate reactors. The amount of UV radiation, preferably UVC radiation, that is directed onto the fluid is dependent upon both the amount of UV light flux of the LED array but also upon how many plate reactors the fluid is directed through (referred to as "residence time"). It has been found by the inventors that directing the fluid stream through channels of a generally consistent small diameter, which can, for example be approximately 4 mm, provides sufficient, and preferably optimal, dosing for sterilization purposes.

In one embodiment, the disclosed UV reactor is adapted to run in a continuous mode, i.e., not in a batch mode. In this embodiment, the sterilization method is a continuous flow system that provides a more efficient and effective sterilization process. Some sterilization reactors achieve a desired dose in a batch mode by irradiating fluid for a certain length of exposure time, and then stopping the irradiation exposure. Instead, embodiments of the UV reactor disclosed herein provide control of the dose in a continuous system that does not need to be turned off to achieve required dosing. The avoidance of down time enables higher sterilization throughput. It is noted that all of the fluid contact materials used are approved by the FDA (Food and Drug Administration).

Figure 1:
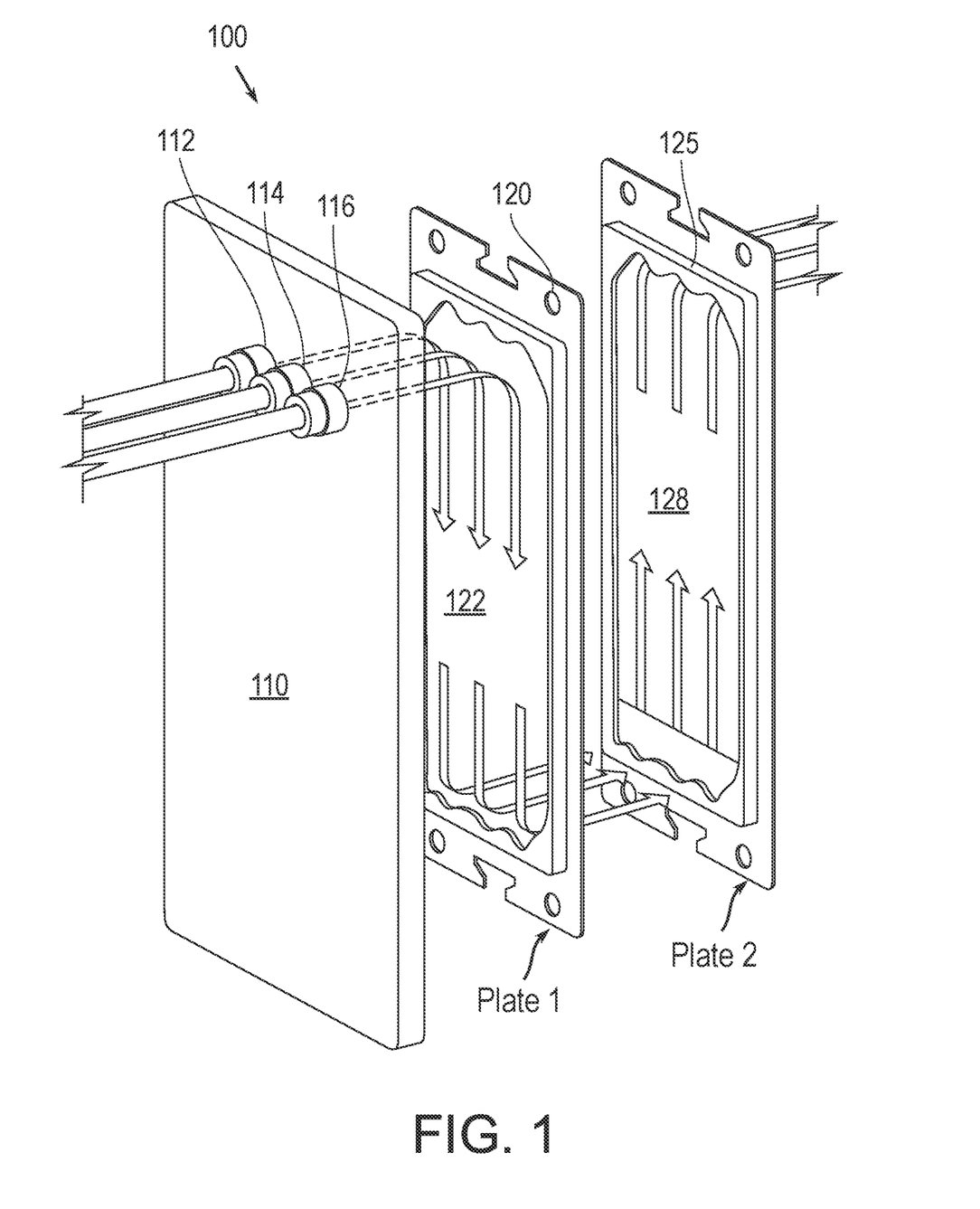
FIG. 1 is a perspective view of a section of a UV reactor system depicting two plate reactors arranged in series with unidirectional flow channels according to an embodiment of the present disclosure.

The plate reactors can comprise a corrugated metal plate with multiple fluid channels, or a single channel compressed in a frame. The UV radiation source is positioned on one side of the channel(s) within the plate reactors, while the liquid to be sterilized flows on the opposite side of the channel within the plate reactor. A cooling system can be coupled to the UV radiation source. The cooling system can use liquid or air to dissipate the heat generated from the UV radiation source. FIG. 1 is a perspective cut-away view of a section of a UV reactor 100 according to an embodiment of the present disclosure depicting an inlet end 110 of the housing and two plate reactors 120, 125 arranged in series. The number of plates shown is merely illustrative and the UV reactor typically includes more than two plates but can also include fewer plates. Plate reactors 120, 125 are arranged in a series along a longitudinal axis that defines the direction in which fluids flow through the UV reactor. In some embodiments, the spacing between the plate reactors can be between 4 mm to 10 mm, but larger or smaller spacings are possible. The plate reactors 120, 125 can be corrugated and include multiple channels, or alternatively, the plate reactors can include a single channel through which the fluid to be sterilized flows in a direction substantially transverse to the longitudinal axis of the UV reactor.

In the embodiment depicted in FIG. 1 there are three inlet ports 112, 114, 116 on the inlet end of the housing 110. A stream of fluid to be sterilized flows through each port. The fluid to be sterilized is also referred to as the "product" flow herein. Each stream of fluid flows unidirectionally from the inlet end 110 downwardly (in a transverse direction with respect to the longitudinal axis) through the first plate reactor 120 where the fluid is exposed to UV radiation in the exposure area 122 of the first plate reactor 120 and sterilized. Fluid emerging from the bottom of plate reactor 120 flow for a distance longitudinally under fluid pressure and then upwardly through the second plate reactor 125 where the fluid is exposed again to UV radiation in the exposure area 128 of the second plate reactor 125 and sterilized further. Thus, the fluid that enters the reactor through inlet ports 112, 114, 116 undergoes considerable exposure to radiation in a series of plate reactors with UV light sources along its longitudinal path through the UV reactor.

Figure 2:
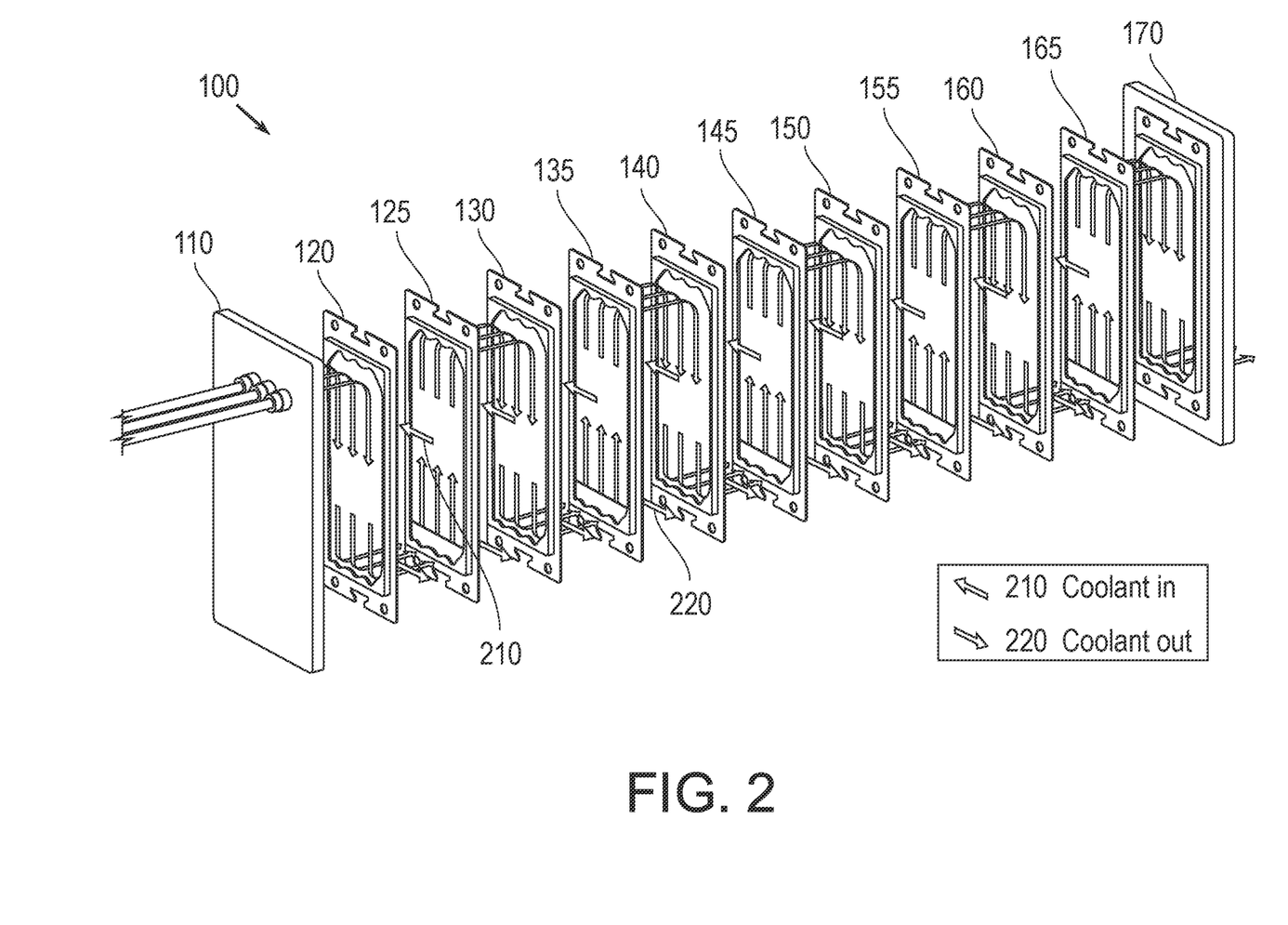
FIG. 2 is a further perspective view of the embodiment of a UV reactor system showing a total of ten plates assembled in a series with a single channel flow. The fluid passes through each plate in a sequential order as it is exposed to the UV irradiance.

FIG. 2 is a perspective cut-away view that depicts an entire embodiment of a UV reactor of which a section is shown in FIG. 1. The UV reactor 100 shown in FIG. 2 includes ten plate reactors 120, 125, 130, 135, 140, 145, 150, 155, 160, 165 arranged in series along a longitudinal axis within a housing (not shown in the cutout view). The fluid entering the UV reactor 100 passes through each plate reactor 120-165 in a sequential order and is exposed to UV irradiance in each plate reactor. In the embodiment depicted, each plate reactor 120-170 includes a single channel through which the fluid is transported and exposed to UV radiation. The total irradiance provided by the plate reactors 120-165 is calibrated and set to achieve a dose required for complete sterilization of the fluid. Fully sterilized fluid that has flowed through plate reactors 120-170 exits through exit ports on outlet end 170 of the housing of the UV reactor. To achieve desirable throughput of fluids through the reactor, flow rates of between 10 and 1000 gallons per minute are used, depending on the size of the reactor and the desired application.

Each of the end plates includes inlets and outlets that couple to external infrastructure for receiving and output product fluids for sterilization. UV light sources generate heat, and the heat will affect the longevity of the source. Therefore, the UV light source requires cooling during operation. To cool the LEDs and provide for adequate heat transfer, a coolant fluid is also circulated through the UV reactor in a countercurrent manner different from and in some cases opposite to the direction of fluid of the product stream. FIG. 2 also depicts this circulation of coolant schematically. In the depicted embodiment, cold coolant 210 enters the UV reactor at the top of the figure and proceeds initially horizontally and then vertically in a top-to-bottom direction via respective cold fluid inlet orifices of the plates. The flow can equally be bottom-to-top in other embodiments. As the cold fluid 210 proceeds through the backside of UV reactor, it cools the UV LEDS. The coolant to which heat from the UV LEDS has been transferred exits at the bottom of the rear of the reactor. Each plate reactor 120-165 includes respective inlets and outlets for coolant flow in addition to product flow.

Figure 3:
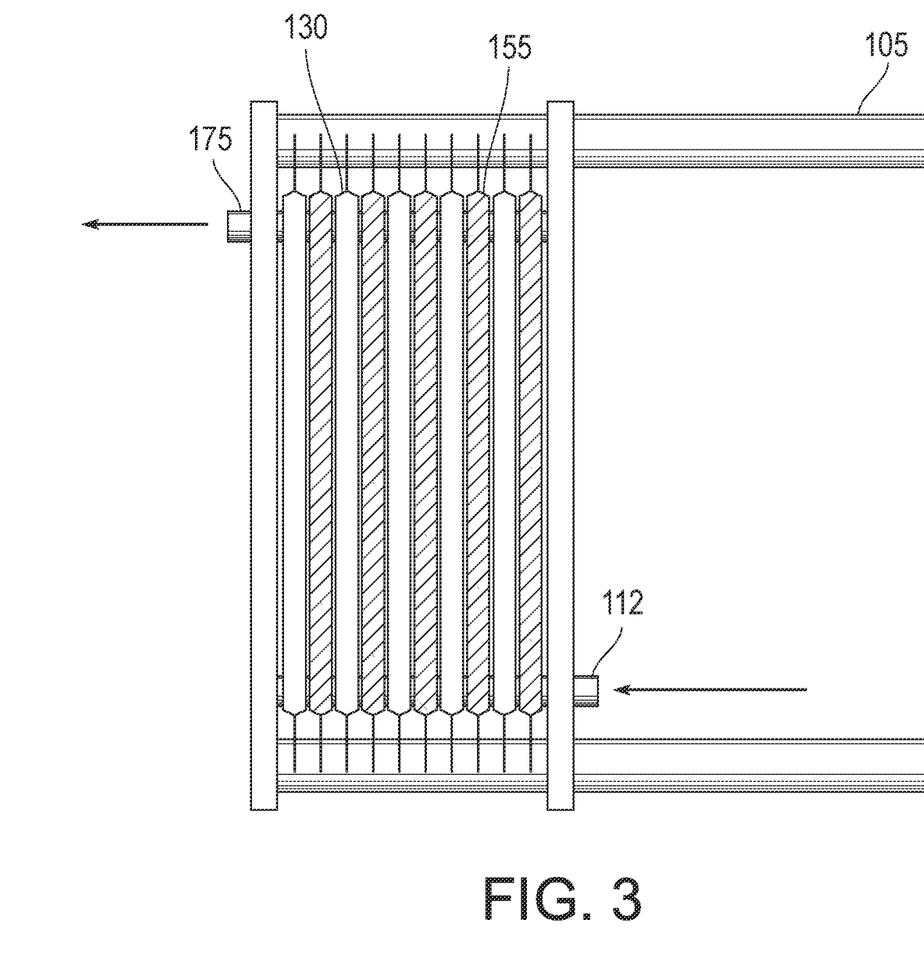
FIG. 3 is a side view of an exemplary arrangement of plate reactors for flow in single channel or multiple channels.

A side view of an exemplary arrangement of plate reactors for flow in single channel or multiple channels is shown in FIG. 3. As in the embodiment shown in FIG. 2, ten plate reactors (two of which 130, 155 are labeled for ease of illustration) are assembled in a series on a frame 105 that extends in a longitudinal direction. Fluid to be sterilized enters inlet 112, flows through the plate reactors, and sterilized fluid exits from outlet 175. The plate reactors are modular and can be easily and safely inserted into and dismantled from the reactor frame. The size (and surface area) of the plate reactors can also vary widely depending on the application. Exemplary dimensions, for example, range from 5 ft to 11 ft in height/width. As shown in FIG. 3, plates are assembled vertically in a series that runs in a longitudinal direction between the end plates of the frame.

Figure 4:
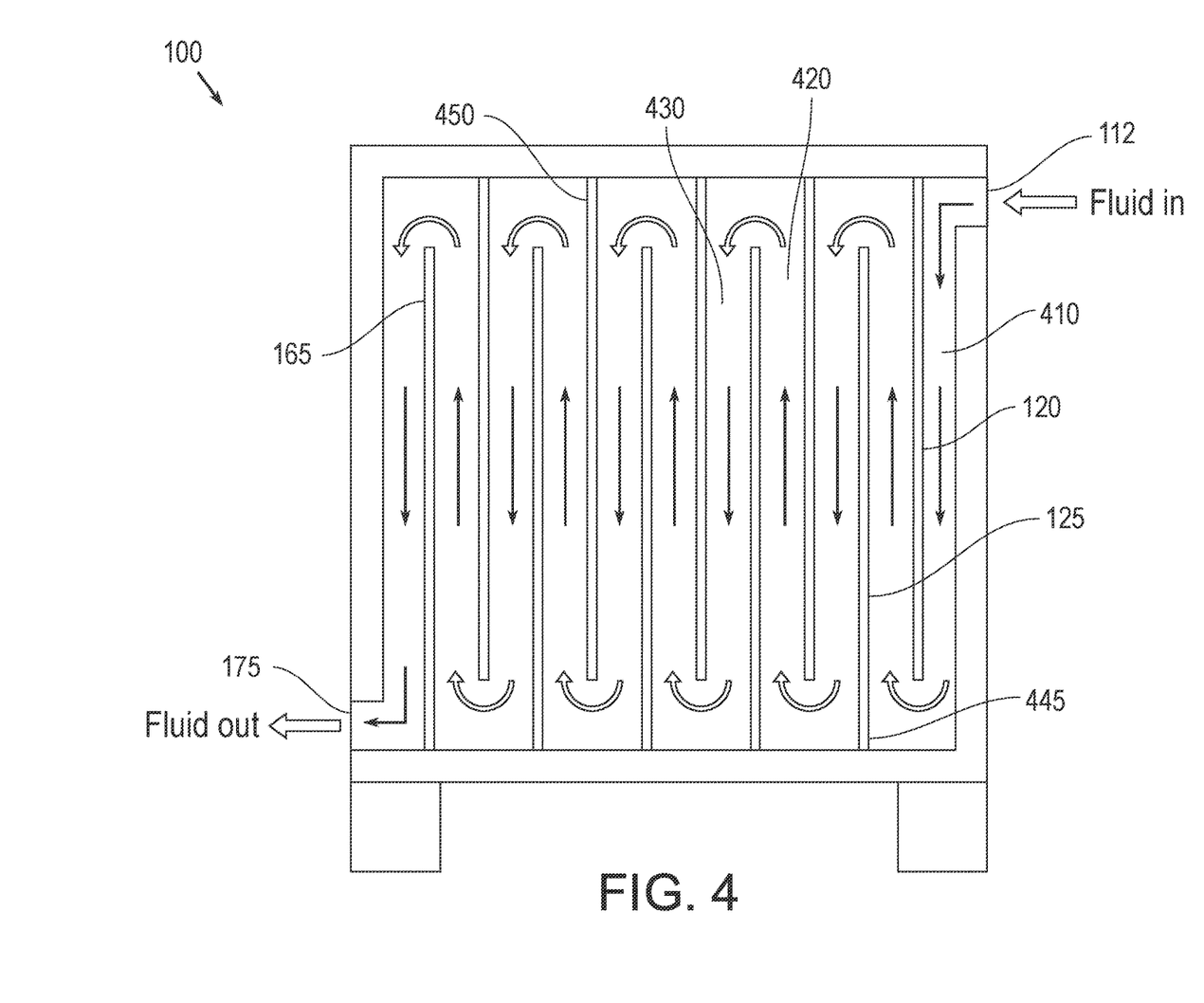
FIG. 4 is a schematic side view that illustrates product fluid flow passing through each plate reactor in a sequential order and being exposed to the UV radiance.

FIG. 4 is a schematic side view that illustrates fluid flow through the UV reactor. As shown, fluids enter the UV reactor at the top of the figure and proceeds longitudinally in a right to left direction through the reactor initially via the respective inlet orifice 112 of the first plate 110. As the fluid proceeds through the UV reactor, the fluid is directed alternatively downwardly and upwardly into channels e.g., 410, 420, 430. For example, after exiting the first plate reactor 120, the fluid is redirected to flow vertically to the top of the second plate 125 where it exits. From the second plate reactor, fluid is conveyed downwardly. This movement is facilitated by baffles e.g., 445, 450 that abut the housing of the reactor and block the fluid from flowing further longitudinally and redirects the flow vertically. The baffles can be parts of the can be extensions from the plate reactors as shown, or that can be separate components that redirect flow. Fluid that exits the last plate 165 is directed to a fluid outlet 175 and outside of the UV reactor.

Figure 5:
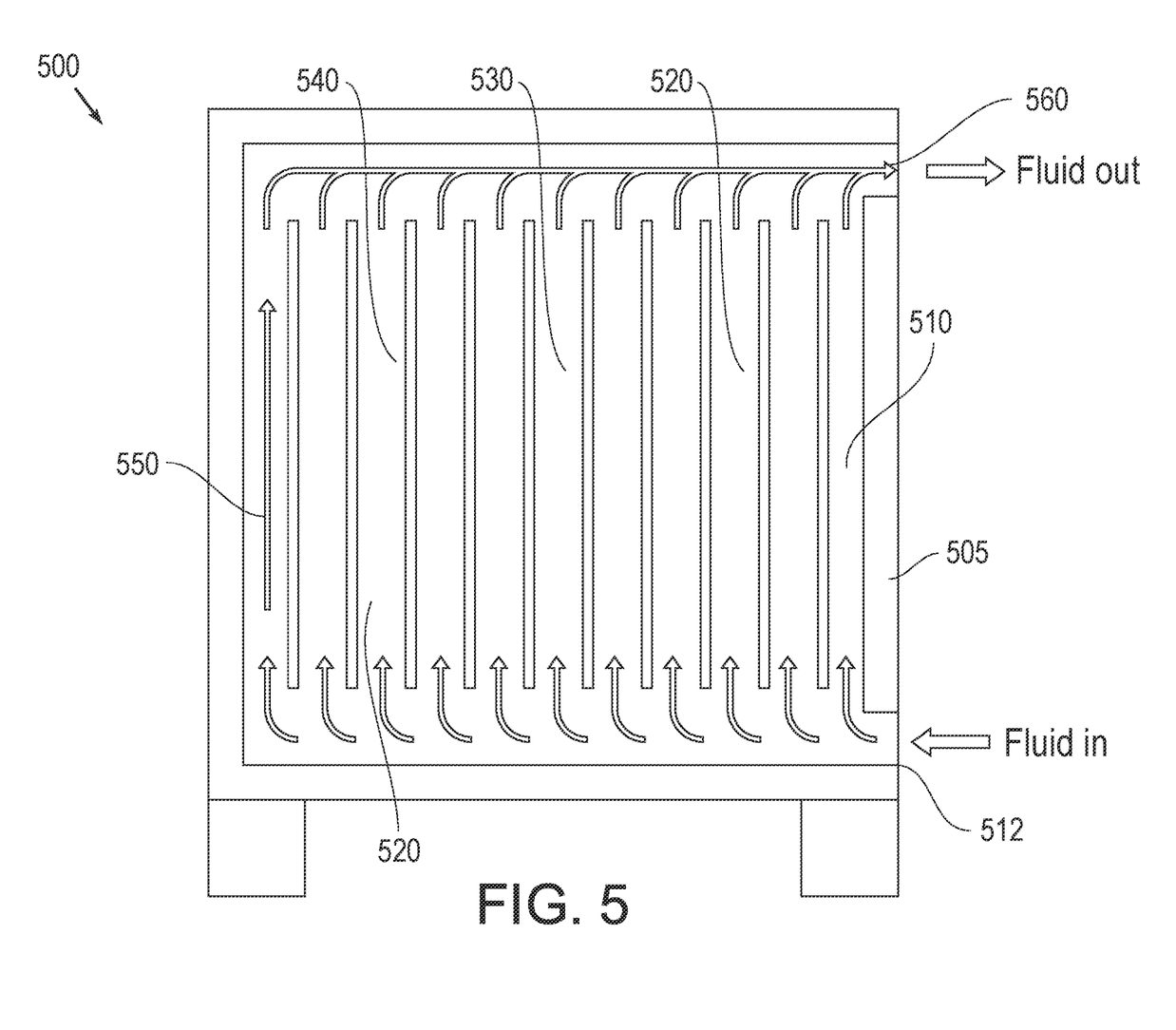
FIG. 5 is a schematic side view of a UV reactor according to another embodiment of the present disclosure.

FIG. 5 is a schematic side view of a UV reactor according to the present disclosure that has an alternative design. In this UV reactor 500, fluid to be sterilized enters a bottom inlet 512, and travels horizontally along the bottom of housing 505 to the end of the reactor. When the bottom of the reactor is filled with fluid, the liquid enters channels between the plate reactors e.g., 520, 530 and the two channels 510, 550 located at the longitudinal ends of the reactor between the plate reactors and the housing 505 (in the depicted embodiments there are eleven channels in total). In each of the channels, the fluid is conveyed unidirectionally upwards in a vertical path. After exiting the vertical channels, the liquid travels horizontally along the top of the UV reactor to an outlet 560.

In all the of the above-described embodiments, the number and dimensions of the channels of the plate reactors are designed to provide a desired radiation exposure and residence time. For example, in some implementations it is desired that the channel diameter be approximately 3-5 millimeters and that the residence time within each plate range between 30 second and 1.5 minutes. It is of course noted that these are exemplary parameters that can be adjusted with the aim of providing a sufficient dose to achieve fluid sterilization.

As previously noted, the radiation sources are preferably LEDs that emit radiation in the ultraviolet range of the EM spectrum, and more preferably in the UVC range, which as noted previously, is the range of wavelengths between 100 and 280 nanometers of the electromagnetic spectrum. In certain embodiments, the plate reactors are corrugated and include grooves or slots or a single channel that can range from 4 mm to 11.5 mm in depth. The slots of the plates can contain numerous UV LEDs or a single channel with numerous UV LEDs. For example, each slot can include on the order of 100 LEDs, although a greater or lesser number of LEDs can be employed depending on the desired application.

The LED-to-LED spacing in the reactor relative to the channels in which the LEDs are situated is an important parameter for achieve desired irradiance. An LED distance-to-height ratio (DHR) is defined as the ratio of the distance between two adjacent LEDs and the height of the channel. The DHR is determined by the area of the channel so as to provide the required irradiance to sterilize the fluid. The light refracted at the surface of the quartz sheath provides an irradiance pattern on a target plane of the fluid, allowing for the generation of a uniform radiance distribution.

Figure 6:
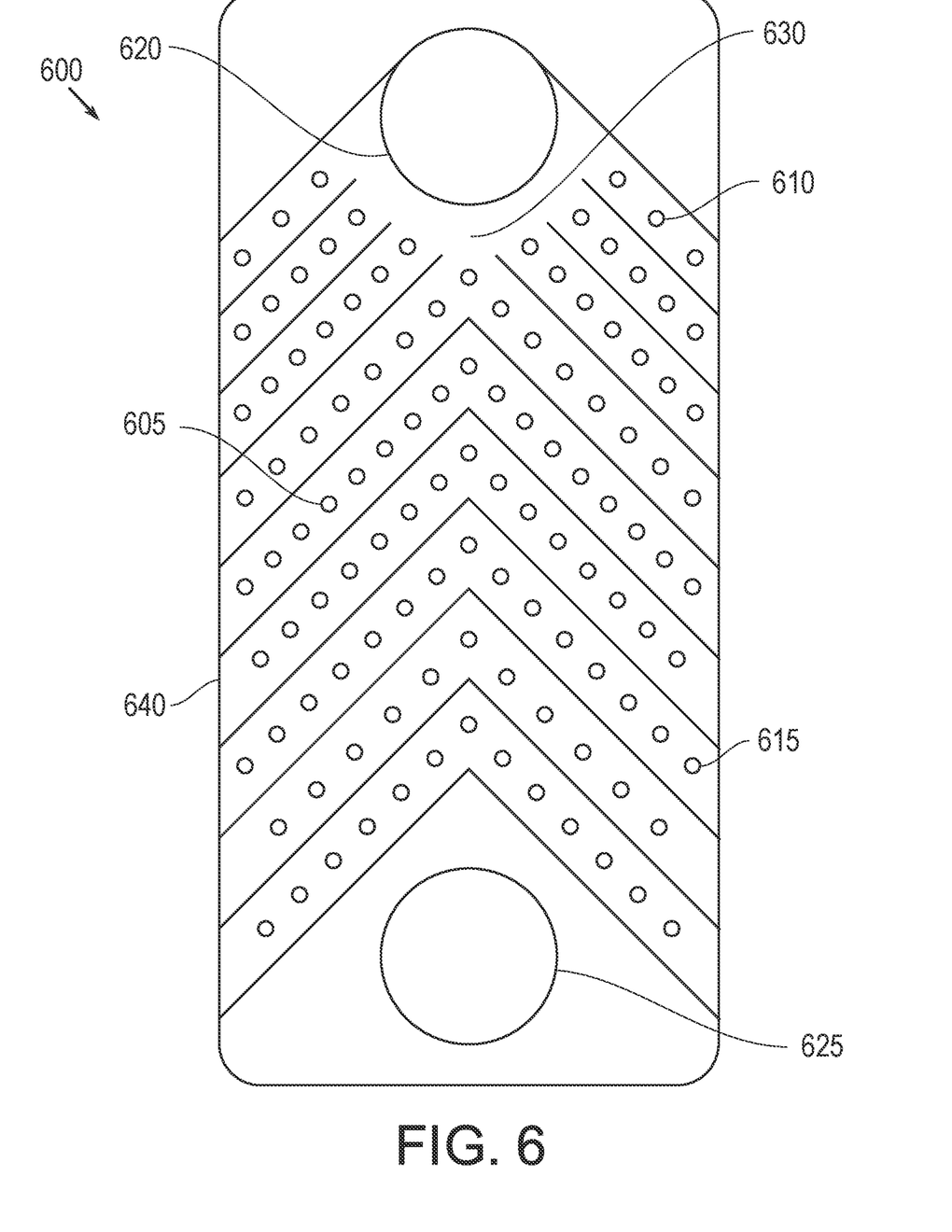
FIG. 6 is a plan view of an embodiment of an individual UV plate reactor according to the present disclosure that has a fishbone design

FIG. 6 is a plan view of an embodiment of an individual UV plate reactor according to the present disclosure. The depicted embodiment includes channels arranged in a fishbone design. The plate reactor 600 includes an elastomer gasket sealing system, as well as the UV LED light sources e.g., 605, 610, 615 incorporated on the plates according to an embodiment of the present disclosure. The plate reactor 600 includes inlets and outlets/openings (referred to herein as orifices) to external infrastructure for the product to enter and exit. For example, the plate reactor shown in FIG. 6 shows the top orifice 620 in which the product fluid enters. Fluid entering the top orifice 620 flows downwards through channels to the bottom orifice 625 at which the fluid exits. Fluid is directed through channels., e.g., 630 formed by the fishbone design. The orifices 620, 625 are preferably aligned with those of other plate reactors positioned in the reactor. The outer edge of the plate reactor can comprise an elastic gasket 640 that forms a peripheral sealing. The gasket sealing prohibits the fluid flow between the plate reactors outside of the channels intended for fluid flow. Each plate reactor can be equipped with additional sealings e.g., 650 that also serve to keep the fluid within the channels. The material and design of the sealings are selected based on the liquid to be treated and can be implemented in a number of ways including, for example, elastomer gaskets to laser welds.

As noted, the UV reactor and ultraviolet sterilization method of the present disclosure employs a modular approach that allows each part of the UV reactor assembly to be changed as needed. Plate reactor units can be added or removed for a new duty, and plate reactors and other components can be easily modified by the user to accommodate expanded capacity requirements. Upon being dismantled, the plate reactors can be cleaned and inspected to the rigorous standards required by the food processing, dairy, and pharmaceutical industries. The plate reactors are preferably formed using hygienic materials such as stainless steel. Similarly, sealing materials are also formed using suitable hygienic materials in areas that come into contact with foods. The gap between the UV light source and the fluid path through the plate reactors can also be adapted for wider separation to handle relatively viscous fluids or fluids with particulates.

Figure 7:
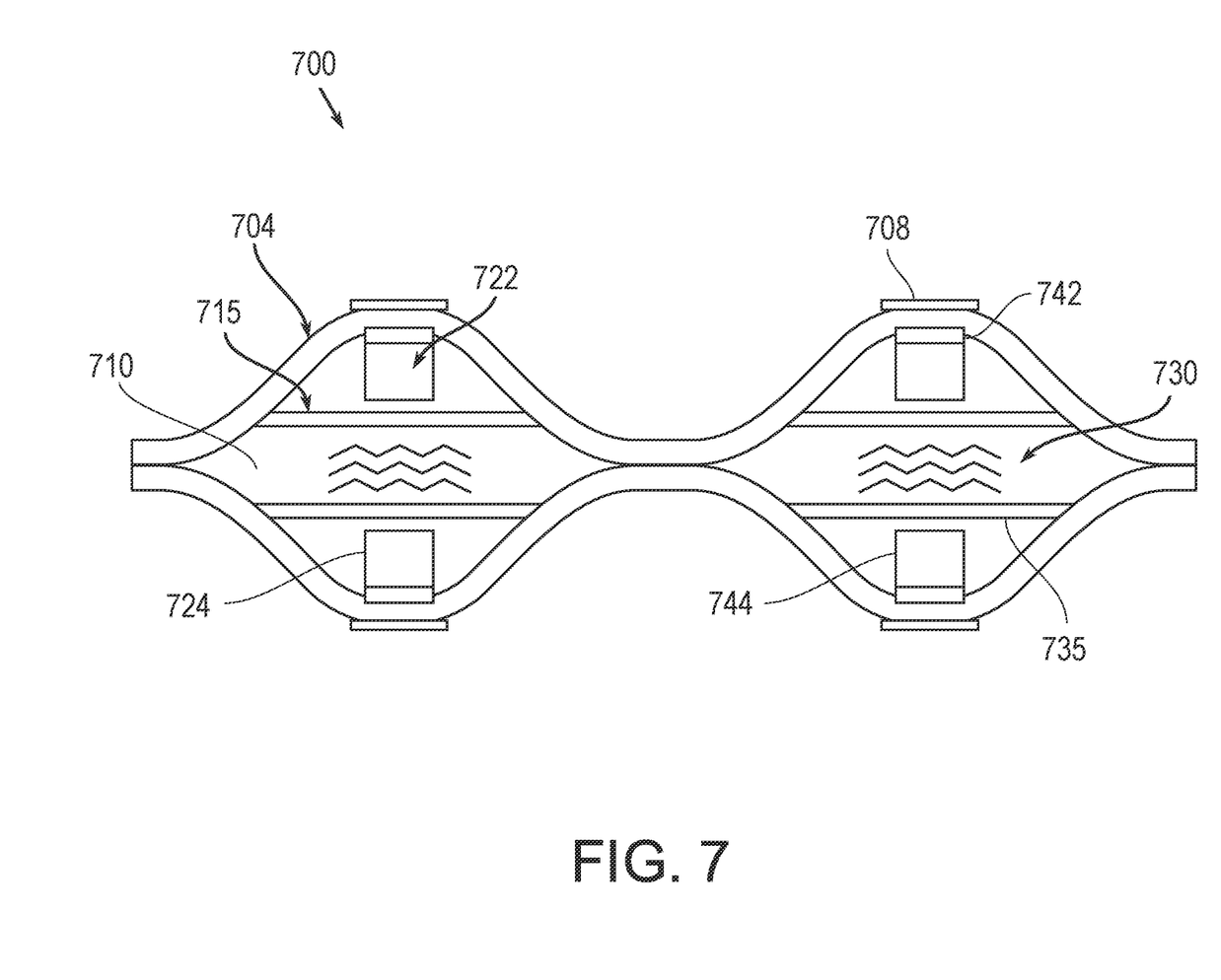
FIG. 7 is a cross-sectional view of a section of an example plate reactor according to the present disclosure in which multiple fluid channels are irradiated from multiple sides.

FIG. 7 is a cross-sectional view of a section of an example plate reactor 700 in which multiple fluid channels are irradiated from multiple sides. The section of the plate reactor is formed of plate sections welded or otherwise joined in such manner that two eyelets 704, 708 are formed between the plates. A first fluid channel 710 flows through the first eyelet 704. The fluid channel 710 is confined within a quartz sleeve 715. The quartz sleeve 715 is substantially transparent to UV radiation. First and second UV radiation sources 722, 724 are positioned on opposite sides of the quartz sleeve 715 within eyelet 710. UV radiation emitted from both UV light sources 722, 724 passes through the quartz sleeve and thus fluid within channel 710 is exposed to radiation emitted from both sources 722, 724. Similarly, a second fluid channel 730 flows through the second eyelet 708. Fluid channel 730 is confined within a second quartz sleeve 735. Third and fourth UV light sources 742, 744 are positioned on the opposite side of quartz sleeve 735 and UV radiation from both sources 742, 744. Fluid within second channel 730 is thereby exposed to radiation emitted from sources 742, 744. The UV radiation sources 722, 724, 742, 744 are protected from contact with fluids by both the quartz sleeves and the plates (e.g., stainless steel).

Figure 8:
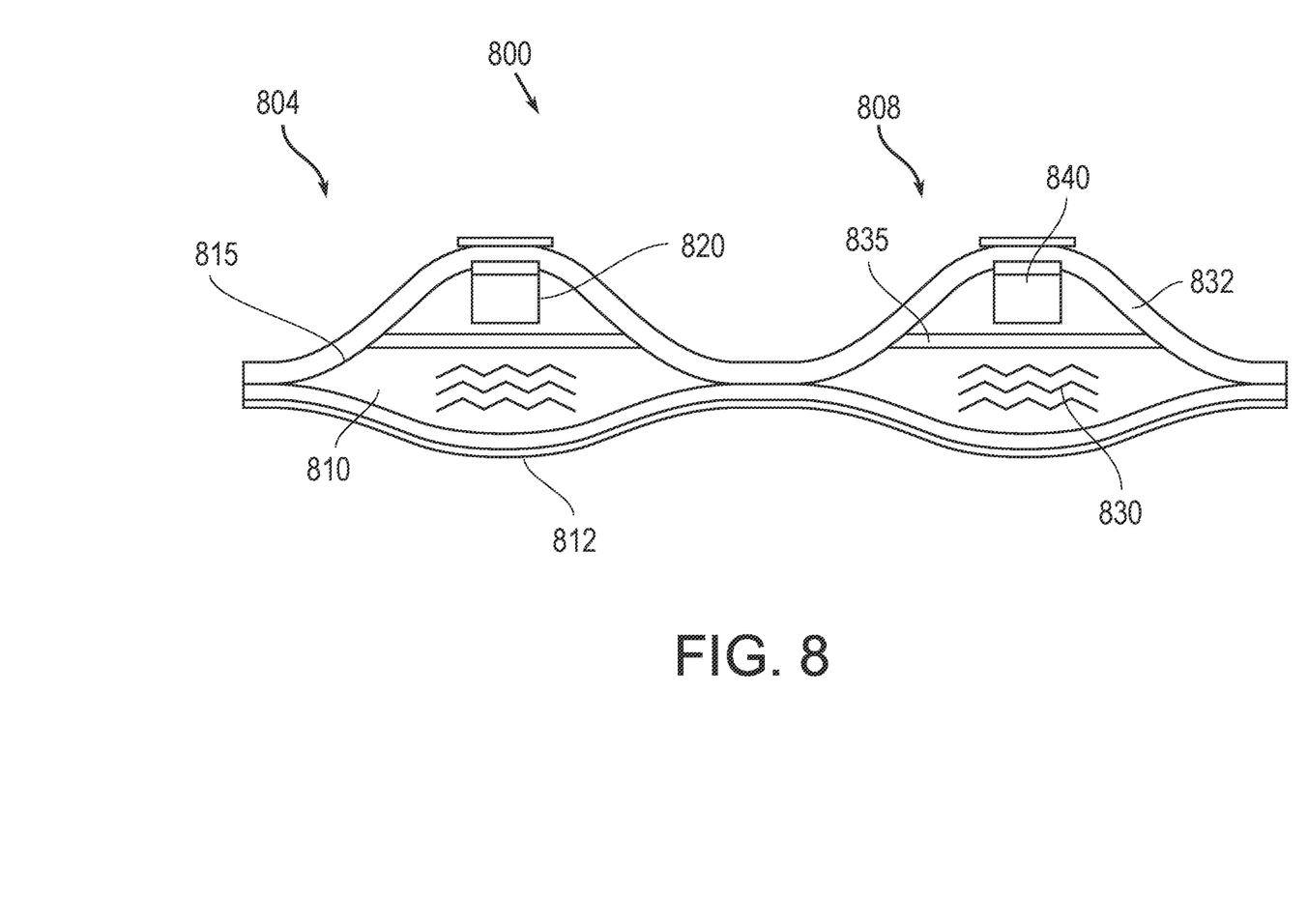
FIG. 8 is a cross-sectional view of a section of an alternative embodiment of a plate reactor according to the present disclosure in which multiple fluid channels are irradiated on one side.

FIG. 8 is a cross-sectional view of a section of an alternative embodiment of a plate reactor 800 in which multiple fluid channels are irradiated on one side. The section of the plate reactor is, like the embodiment shown in FIG. 2, formed of plate sections welded or otherwise joined in such manner that two eyelets 804, 808 are formed between the plates. However, the eyelets 804, 808 in this embodiment are asymmetrical unlike those shown in FIG. 7. A first fluid channel 810 flows through the first eyelet 804. The fluid channel 810 is confined between plate 812 and a quartz sleeve 815. A UV radiation source 820 is positioned on an opposite side of quartz sleeve 815 from the channel 810 irradiates fluid that flows within channel 810. Similarly, a second fluid channel 830 flows through the second eyelet 808. Fluid channel 830 is confined between plate 832 within a second quartz sleeve 835. A second UV radiation source 840 is positioned on opposite side of quartz sleeve 835 from channel 830. The second UV radiation source 840 irradiates fluid that flows within channel 830.

Figure 9:
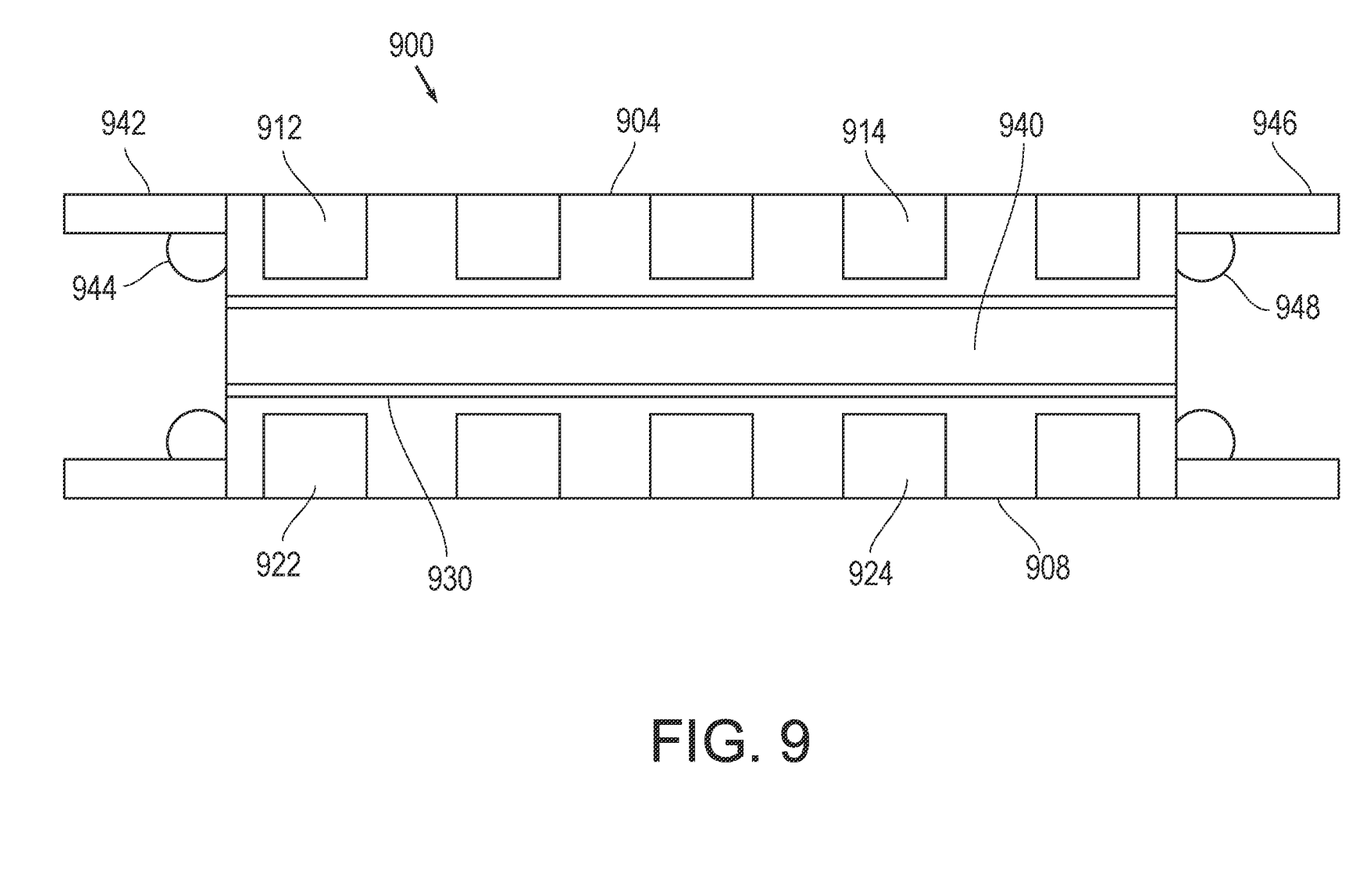
FIG. 9 is a cross-sectional view of a section of a further embodiment of a plate reactor in which a single fluid channels is irradiated on multiple sides.

FIG. 9 is a cross-sectional view of a section of a further embodiment of a plate reactor 900 in which a single fluid channels is irradiated on multiple sides. The plate reactor 900 includes first and second plates 904, 908 positioned parallel to one another. A first set of UV LEDs e.g., 912, 914 is positioned on the first plate 904 in the area between the plates, and a second set of LEDs e.g., 922, 924 are positioned opposite to the first plurality of LEDs on the second plate 908. Positioned between the first and second sets of UV LEDs is a quartz sleeve 930 that surrounds a fluid channel 940. As fluid flows through the channel 940 it is irradiated by both the first and second sets of UV LEDs. The plate reactor 900 includes a first flange 942 and gasket 944 at a first end, and a second flange 946 and gasket 948 at a second end. The flanges and gaskets provide a peripheral sealing for control of fluid flow and fixtures that enable the easy installation and removal of the plate reactors within the UV reactor. In this embodiment as in others, the UV radiation sources are separated from the liquid flow by the plate (e.g., stainless steel) and the quartz sleeve.

Figure 10:
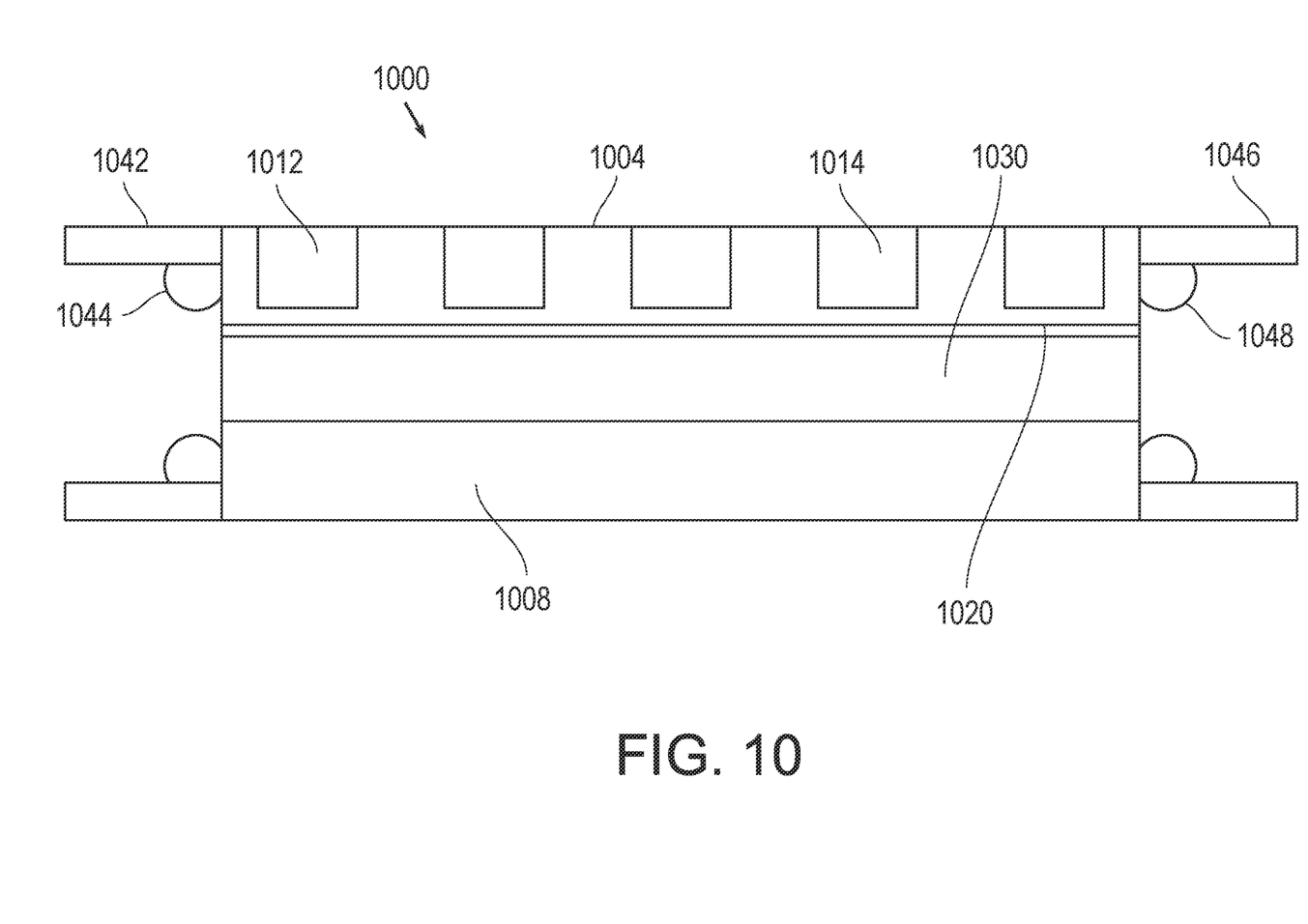
FIG. 10 is a cross-sectional view of a section of a further embodiment of a plate reactor in which a single fluid channels is irradiated on a single side.

FIG. 10 is a cross-sectional view of a section of an embodiment of a plate reactor 1000 in which a single fluid channel is irradiated on a single side. The plate reactor 1000 includes an irradiation plate 1004 upon which a set of UV LEDs e.g., 1012, 1014 is positioned and a base plate 1008. The space between the sleeve 1020 and base plate 1008 defines a fluid channel 1030. As fluid flows through the channel 1030, it is irradiated by the set of UV LEDs e.g., 1012, 1014. The plate reactor 1000 includes a first flange 942 and gasket 944 at a first end, a second flange 946 and gasket 948 at a second end. The flanges and gaskets provide a peripheral sealing for control of fluid flow and fixtures that enable the easy installation and removal of the plate reactors within the UV reactor. In this embodiment as in others, the UV radiation sources are separated from the liquid flow by the plate (e.g., stainless steel) and the quartz sleeve.

The disclosed UVC reactor system has several advantages over the related art. The disclosed reactor system provides an enhanced UV irradiation transfer area plate and compact design, resulting in a more efficient sterilization process. There is little to no shadowing as with traditional UV sterilization systems. UV light travels in a straight line, so any shadow or obstruction will reduce its efficiency. The design of the present disclosure eliminates shadowing and exposes the entire liquid to irradiation.

Sterilization "lethality" can be efficiently and effectively increased simply by adding more modular plates to the frame structure. Traditional systems will require a complete redesign of the plasma discharge lamps and construction of a new system. Moreover, the reactor can be adapted easily and inexpensively to sterilize different types of products with different sterilization specifications. In addition, the reactor design provides more effective cooling of the UV light source which helps extend the light of life of the light sources.

In addition, the ultraviolet sterilization reactor and method disclosed herein does not require the removal of oxygen from the fluid prior to irradiation, nor does it require the presence of nitrate nitrogen to effectively sterilize the liquid. The method additionally does not require a temperature range limit for the liquid during sterilization.

It is to be understood that any structural and functional details disclosed herein are not to be interpreted as limiting the systems and methods, but rather are provided as a representative embodiment and/or arrangement for teaching one skilled in the art various ways to implement the methods. It is to be further understood that like parts in the drawings represent like elements through the several figures, and that not all components and/or steps described and illustrated with reference to the figures are required for all embodiments or arrangements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to a viewer. Accordingly, no limitations are implied or to be inferred.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the disclosure as understood by a person having ordinary skill in the art.

What is claimed is:

1. An ultraviolet (UV) reactor for sterilizing a stream of fluid comprising:
   a fluid input port and a fluid output port;
   a frame structure having a longitudinal dimension; and
   a plurality of plate reactors that are removably insertable into the frame structure in a series interposed between the fluid input port and the fluid output port and extending along the longitudinal dimension of the frame structure, each of the plurality of plate reactors including at least one channel into and through which the stream of fluid is transported in a direction transverse to the longitudinal dimension of the frame structure; and
   at least one ultraviolet light source having a selected radiant flux is positioned to irradiate the at least one channel and the stream of fluid therein, wherein the stream of fluid at the fluid output port is sterilized.

2. The reactor of claim 1, wherein a diameter of at least on channel and the radiant flux of the ultraviolet light source are selected so as to provide a selected dosage of ultraviolet radiation to the stream of fluid in a confined space of the at least one channel so as to obtain sterilization of the stream of fluid.

3. The reactor of claim 1, wherein the diameter of each of the at least one channel is between 3 mm and 10 mm.

4. The reactor of claim 1, wherein the ultraviolet light source comprises a plurality of light emitting diodes (LEDs) that radiates in a UVC spectral range.

5. The reactor of claim 4, wherein each of the plurality of plate reactors include a quartz sleeve and a housing that separates fluid within the at least one channel from the plurality of LEDs that irradiate the fluid.

6. The reactor of claim 1, wherein a coolant is transported through the reactor to cool the plurality of LEDs.

7. The reactor of claim 1, wherein the frame and plate reactors are composed of stainless steel.

8. The reactor of claim 1, wherein the plurality of plate reactors each include multiple channels for transport of fluid to be sterilized.

9. The reactor of claim 1, wherein each of the plurality of plate reactors includes a sealing system adapted to stream of fluid to be treated for confining the stream of fluid within the at least one channel.

10. The reactor of claim 9, wherein the sealing system includes an elastomer gasket.

11. The reactor of claim 9, wherein the sealing system includes a laser weld.

12. An ultraviolet (UV) reactor for sterilizing a stream of fluid comprising:
    a frame structure having a longitudinal dimension; and
    a plurality of plate reactors that are removably insertable into the frame structure in a series extending along the longitudinal dimension of the frame structure, each of the plurality of plate reactors including:
       at least one channel into which the stream of fluid is transported,
       a quartz sleeve and housing, and
       an ultraviolet light source having a selected radiant flux is positioned to irradiate the at least one channel that is separated from the fluid within the at least one channel by the quartz sleeve and housing,
    wherein the ultraviolet light source comprises a plurality of light emitting diodes (LEDs) that radiates in a UVC spectral range.

* * * * *